US00PP15000P2

(12) United States Plant Patent
Olesen et al.

(10) Patent No.: US PP15,000 P2
(45) Date of Patent: Jul. 6, 2004

(54) COMPACT FLORIBUNDA ROSE PLANT NAMED 'POULAC017'

(50) Latin Name: *Rosa hybrida*
Varietal Denomination: POULac017

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/672,351

(22) Filed: Sep. 25, 2003

(51) Int. Cl.[7] ..... A01H 5/00
(52) U.S. Cl. ..... Plt./145
(58) Field of Search ..... Plt./145

*Primary Examiner*—Bruce R. Campell
*Assistant Examiner*—Annette H Para

(57) ABSTRACT

A new compact floribunda rose plant which has abundant, light yellow to near white flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULac017'.

SUMMARY OF THE INVENTION

The present discovery constitutes a new and distinct variety of a compact floribunda pot rose plant which was discovered in a cultivated area. The mutation resulted from 'POULra015', a miniature pot rose hybridized by the same inventors. 'POULra015' is described and illustrated in U.S. Plant Pat. No. 14,309, and applied for on Sep. 17, 2002. The new rose variety resulted from a naturally occurring mutation of unknown causation on a branch of 'POULra015'.

The rose plant of the present discovery has a unique combination of characteristics which are outstanding in the new variety and which distinguish it from the original rose 'POULra015' as well as all other varieties which we are aware of. For example, the new variety has:

1. Uniform and abundant near white to light yellow flowers with rose fragrance;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULac017' from all other varieties of which we are aware.

The resulting mutation was selected and evaluations were conducted on the resulting rose plants in a controlled environment.

Asexual reproduction of 'POULac017' by cuttings and traditional budding was first done by L. Pernille and Mogens N. Olesen in their nursery in Fredensborg, Denmark in 1999. This initial and other subsequent propagations conducted in controlled environments have demonstrated that the characteristics of 'POULac017' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac017'. Specifically illustrated in FIG. 1:

FIG. 1.1; Opened flower;

FIG. 1.2; Flower bud, closed, partially open and ¼ open;

FIG. 1.3; Flower petals, detached;

FIG. 1.4; Sepals, receptacle, and pedicel;

FIG. 1.5; Juvenile leaves;

FIG. 1.6; Leaves.

FIG. 1.7; Bare stem.

DETAILED DESCRIPTION OF THE VARIETY

The following is a description of 'POULac017', as observed in its growth in glasshouses in, Burlington Ontario. Observed plants were grown for 10 months in 15 cm pots. Color references are made using The Royal Horticultural Society (London, England) Colour Chart, 1995, except where common terms of color are used.

For a comparison, several physical characteristics of the rose variety 'POULgret', a rose variety from the same inventors described and illustrated in U.S. Plant Pat. No. 10,729 and issued on Dec. 22, 1998, are compared to 'POULac017' in Chart 1.

CHART 1

| | 'POULac017' | 'POULgret' |
|---|---|---|
| Petal Color | Outermost Petals: | Outermost Petals: |
| Open Flower | Yellow Group 11D | White 155B |
| Petal Count | 14 under normal conditions. | 25 to 28 under normal conditions. |
| Petal Spot | None observed. | Yellow Group 4C. |

FLOWER AND FLOWER BUD

Blooming habit: Continuous.

Flower bud:

*Size*.—Upon opening, 22 mm in length from base of receptacle to end of bud.

*Bud form*.—Broad based.

*Bud color*.—As sepals unfold, Yellow Group 8B; Yellow Group 9D at ¼ opening.

*Sepals*.—Upper Surface: Green Group 146B to 145B. Lower Surface: Yellow-Green Group 146B. Anthocyanin: Medium amount. Greyed-Orange Group 176A. Additional Observations: Strong foliaceous appendages on three of the five sepals. Surfaces of sepals slightly pubescent. Stipitate glands are scant. Shape: Sepal apex is cirrose. Base is flat at union with receptacle. Size: 35 mm long×5 mm wide.

*Receptacle*.—Surface: Smooth and glabrous. Shape: Funnel shaped. Size: 6 mm (h)×8 mm (w). Color: Yellow-Green Group 144A. Anthocyanin: None observed.

*Peduncle*.—Surface: Smooth and stipitate glands scant. Length: 75 mm to 90 mm average length. Color: Yellow-Green Group 144A. Strength: Strong.

*Borne*.—Singularly.

*Anthocyanin*.—Strong.

Flower bloom:

*Fragrance*.—Moderate rose scent.

*Duration*.—The blooms have a duration on the plant of approximately 7 to 10 days. Petals fall cleanly away from plant.

*Size*.—Medium for a 15 cm pot rose. Average flower diameter is 40 to 50 mm when open. Average flower depth is 25 mm when open.

*Form*.—Deep Cup. Shape of flower when viewed from the side: Upon opening, upper part: Flat. Upon opening, lower part: Flattened convex. Open flower, upper part: Flat. Open flower, lower part: Flattened convex.

*Petalage*.—Semi double. Average range: 14 petals under normal conditions with 3 petaloids.

Color:

*Upon opening, petals*.—Outermost petals: Outer Side: Yellow Group 8D, middle to marginal zone. Intonations of: Yellow Group 13C at basal zone. Inner Side: Yellow Group 8D, middle to marginal zone. Intonations of 8C to 8A at basal zone. Innermost petals: Outer Side: Yellow Group 8C with intonations of Yellow-Orange Group 22B. Inner Side: Yellow Group 8C with intonations of 8A at basal zone.

*Upon opening, basal petal spots*.—No distinctive coloration at petal base observed.

*After opening, petals*.—Outermost petals: Outer Side: Yellow Group 11D with intonations of Yellow Group 8A at the basal zone. Inner Side: Yellow Group 11D with intonations of Yellow Group 8A at the basal zone. Innermost petals: Outer Side: Yellow Group 8D with intonations of Yellow 8A at the basal zone. Inner Side: Yellow Group 8D with intonations of Yellow 8A at the basal zone.

*After opening, basal petal spots*.—No distinctive coloration at petal base observed.

General tonality: On open flower Yellow Group 8D with intonations of Yellow-Orange Group 14D. No change in the general tonality at the end of the 10th day.

Petals:

*Petal reflex*.—Somewhat.

*Petal edge*.—Entire. Weak and undulations of margin.

*Apex shape*.—Round with point in center of margin.

*Base shape*.—Rounded.

*Size*.—Length 30 mm, width 52 mm.

*Petaloids*.—3 to 5. Petaloids are 25 mm long and 22 mm wide. Petaloid Shape: Irregular. Petaloid Color: Upper surface: Yellow 8C to 8A. Lower surface: Yellow 8C with intonations of Yellow-Orange Group 22B.

*Thickness*.—Average.

*Arrangement*.—Formal.

Reproductive organs:

*Pistils*.—Length: 6 mm long. Quantity: 68 actual count.

*Pollen*.—None observed.

*Anthers*.—Size: 2 mm long. Color: Yellow Group 13C. Quantity: 54 (actual count.)

*Filaments*.—Color: Yellow Group 6C. Length: 4 to 5 mm.

*Stigmas*.—Superior in location to anthers. Color: Greyed-Yellow Group 162D.

*Styles*.—Color: Greyed-Purple Group 58A.

*Seed formation*.—Hips not observed.

PLANT

Plant growth: Vigorous, compact, upright to bushy. When grown as a 15 cm pot plant, the average height of the plant itself is 27 cm and the average width is 18 cm.

Stems:

*Color*.—Young wood: Yellow-Green Group 146A to 146B. Older wood: Yellow-Green Group 146A to 146B.

*Thorns*.—Incidence: None observed.

*Size*.—Average length: 20 cm from flower to first branch. Stem diameter is 3 mm.

*Internodal distance*.—40 mm (average.)

*Surface texture*.—Young wood: Smooth. Older wood: Smooth.

Plant foliage: Typical number of leaflets on leaves in middle of the stem: 5 leaflets.

*Compound leaf size*.—106 mm (l)×73 mm (w).

*Quantity*.—Average, one leaf per each 4 cm of stem.

*Color mature foliage*.—Upper Leaf Surface: Yellow-Green Group 137A to 146A. Lower Leaf Surface: Yellow-Green Group 146C.

*Color juvenile foliage*.—Upper Leaf Surface: Yellow-Green Group 152D. Lower Leaf Surface: Yellow-Green Group 152D.

*Anthocyanin intonation*.—Yes. Location: Juvenile leaves. Color: Greyed-Orange Group 176A.

Plant leaves and leaflets:

*Stipules*.—Size: 7 mm (l) by 2 mm (w). Presence of stipitate glands: Few.

*Petiole*.—Length: 23 mm. Width: 1 mm. Color: Yellow-Green Group 146C. Underneath: Thorns and few stipitate glands.

*Rachis*.—Length: 29 mm. Color: Yellow-Green Group 146C. Anthocyanin: None. Underneath: Thorns and few stipitate glands.

*Leaflet*.—Edge: Finely serrated. Shape: Ovate. Terminal Leaflet Size: 56 mm long×29 mm wide. Vein Color: Yellow-Green Group 146C. Texture: Smooth. Thickness: Medium. Arrangement: Old pinnate. Venation: Reticulate. Leaf surface: Matte finish.

Disease resistance: Above average resistance to mildew, black spot, and Botrytis under normal growing conditions in Burlington, Canada.

We claim:

1. A new and distinct variety of rose plant of the compact floribunda class, substantially as herein illustrated and described as a distinct and novel rose variety due to its abundant, light yellow to near white flowers, vigorous growth, compact habit, suitability for production from softwood cuttings in pots, and durable flowers and foliage which make the variety suitable for distribution in the floral industry.

* * * * *

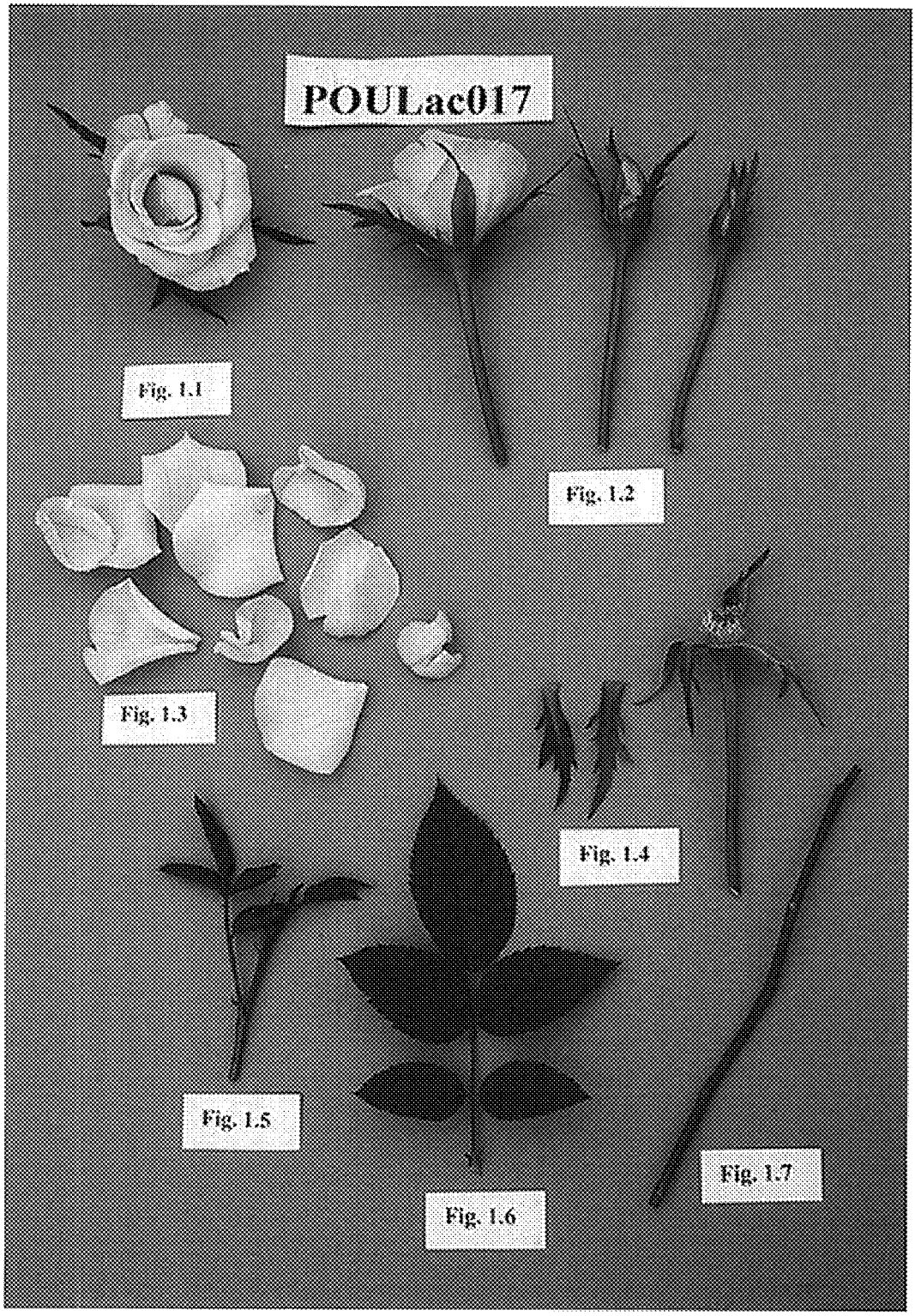
POULac017
Fig. 1.1
Fig. 1.2
Fig. 1.3
Fig. 1.4
Fig. 1.5
Fig. 1.6
Fig. 1.7